United States Patent [19]

Stern et al.

[11] Patent Number: 5,144,069

[45] Date of Patent: Sep. 1, 1992

[54] PROCESS FOR THE PREPARATION OF FLUOROALIPHATIC AMINOCARBOXYLATE SURFACTANTS

[75] Inventors: Richard M. Stern, Woodbury; Richard A. Guenthner, White Bear Lake; Roger R. Alm, Lake Elmo; Thomas K. Wilkinson, Woodbury, all of Minn.

[73] Assignee: Minnesota Mining and Manufacturing Company, St. Paul, Minn.

[21] Appl. No.: 626,739

[22] Filed: Dec. 13, 1990

[51] Int. Cl.$^5$ .............................................. C07C 315/00
[52] U.S. Cl. ................................... 562/556; 252/8.05; 562/430
[58] Field of Search .................. 562/556, 430; 564/96

[56] References Cited

U.S. PATENT DOCUMENTS

| | | | |
|---|---|---|---|
| 2,759,019 | 8/1956 | Brown | 564/96 |
| 2,809,990 | 10/1957 | Brown | 562/556 |
| 2,934,450 | 4/1960 | Brown | 562/556 |

FOREIGN PATENT DOCUMENTS 765256 8/1971 Belgium.

58-201752 11/1983 Japan.

*Primary Examiner*—Michael L. Shippen
*Attorney, Agent, or Firm*—Gary L. Griswold; Walter N. Kirn; Eloise J. Maki

[57] ABSTRACT

A process for the synthesis of the fluorochemical compound having formula $$R_fSO_2N(CHR^2-CHR^2COO^-)R^1N^+(R)_2H$$

wherein $R_f$ is a fluoraliphatic radical containing at least 3 carbon atoms. The synthesis involves reaction of compounds of formula $R_fSO_2N(H)R^1N(R)_2$ and $CHR^2=CH^2COOH$ in solution at elevated temperatures. The process can be used to synthesize the fluoroaliphatic amphoteric amino carboxylate surfactant having the formula:

$$C_6F_{13}SO_2N(C_2H_4COO^-)C_3H_6N^+(CH_3)_2H$$

which compound is useful in aqueous film-forming foamable concentrates for extinguishing flammable liquid fires.

21 Claims, No Drawings

PROCESS FOR THE PREPARATION OF FLUOROALIPHATIC AMINOCARBOXYLATE SURFACTANTS

The present invention relates to a process for the preparation of fluoroaliphatic aminocarboxylate surfactants, for example, N-(2 carboxyethyl)-N-[3-(N',N'-dimethylamino)propyl]perfluorohexane sulfonamide.

Aqueous foaming agents, in particular those yielding aqueous film-forming foams (AFFFs), have become an increasingly important means for extinguishing hydrocarbon and other flammable liquid fires. In view of the importance of fire extinguishing materials there is continuing urgency to improve these materials and the processes by which they are manufactured.

Aqueous film-forming foamable concentrates typically contain fluorochemical surfactants. The concentrates when diluted with water and aerated produce a foam which is particularly effective in extinguishing hydrocarbon and other liquid flammable fires. These foamable concentrates are applied typically by in-line dilution with water passing through a fire hose and aeration, for example, by passing the diluted mixture through an air aspirating nozzle at the outlet end of the hose to form an aqueous film-forming foam which is sprayed directly onto the fire. The fluorochemical surfactants depress the surface tension of the foam to within critical ranges below the surface tension of the fuel so that a vapor sealing film spreads readily over the fuel. The film must have a strong tendency to reform if broken thus reducing the tendency of fires to reignite where the film has been disturbed.

Representative prior art references describing the nature of such fluorochemical surfactant concentrates are described in U.S. Pat. Nos. 3,258,423 (Tuve), 3,562,156 (Francen), 3,772,195 (Francen), 4,359,096 (Berger), and 4,795,590 (Kent).

A particularly useful fluorochemical surfactant for use in such film-forming foamable concentrates is a fluoroaliphatic amphoteric surfactant which is a fluorinated aminocarboxylate having the following structure (shown in its zwitterion form):

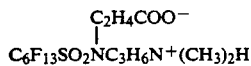

N-(2-carboxyethyl)-N-[3-(N',N'-dimethylamino)-propyl]perfluorohexane sulfonamide. The sodium salt of this compound is disclosed in U.S. Pat. No. 4,536,298 (Kamei) at col. 3, lines 62–64.

Known prior art methods for synthesizing this compound from fluoroaliphatic amides employ ring-opening reactions of lactones, e.g. propiolactone, or condensation reactions utilizing chloropropionic or chloroacetic acids in the presence of base. Ring-opening lactone synthesis routes are described for example in U.S. Pat. No. 3,661,776 (Fletcher) at col 3 Methods of synthesis employing ring-opening reactions of lactones are very difficult and hazardous to effect commercially, since such lactones are suspected carcinogens. Also, synthesis involving displacement of chloride from chlorocarboxylic acids (e.g. chloropropionic acid or chloroacetic acid) gives residual chloride ion by-product which can cause pitting and corrosion of stainless steel containers and equipment used with AFFF compositions.

U.S. Pat. No. 3,536,749 (Groves) teaches the reaction of an ester of acrylic acid or ester of methacrylic acid with a fluorocarbon amide having at least one hydrogen atom bonded to the amide nitrogen. The amide nitrogen can be a sulfonamide. The reaction is carried out in the presence of a highly basic catalyst such as benzyltrimethyl ammonium hydroxide at temperatures between about 80° to 150° C. This reference does not disclose applicant's reactions or process which preferably is carried out without catalyst and involves preferential addition of acrylic acid to the sulfonamido nitrogen in the presence of a competing amino reaction site with little or minimal addition of acrylic acid to this competing tertiary amino reaction site.

U.S. Pat. No. 4,069,158 (Bertocchio) discloses reaction of acrylic acid with a fluoroaliphatic compound containing both a sulfonamido group and a tertiary amino group. The reaction is carried out at room temperature and shows reaction of acrylic acid only at the tertiary amino site yielding a quaternary ammonium carboxylate product of about 93% yield. This reference does not disclose reaction of acrylic acid at the sulfonamido nitrogen site and does not disclose applicant's process.

The novel process of the present invention is directed in a principal aspect to the synthesis of the class of fluorochemical compounds represented by the formula:

Where $R_f$ is a fluoroaliphatic radical (e.g. $C_6F_{13}$—), R and $R^1$ are organic radicals or groups such as alkyl (e.g. methyl) and alkylene (e.g. propylene), respectively, and $R^2$ is H or $CH_3$. $R_f$, R, and $R^1$ are defined in more detail later in this application. The synthesis of this compound involves a condensation reaction (a) of compounds of formulas $R_fSO_2F$ and $H_2NR^1N(R)_2$ to produce an intermediate compound of formula $R_fSO_2N(H)R^1N(R)_2$. This intermediate compound is then reacted with $CHR^2=CR^2COOH$ in an addition reaction (b) to yield the by-products. The desired compound (I) and reaction condensation reaction (a) can be carried out in solution at reaction temperature of above 80° C., preferably between about 80° C. and 95° C., and the addition reaction (b) can be carried out at reaction temperatures of above 90° C., preferably between about 90° C. and 150° C.

Suitable solvent can be used to solubilize all the reactants and products in the condensation reaction, and subsequent distillation can be used to remove the solvent leaving a liquid phase rich in intermediate compound $R_fSO_2N(H)R^1N(R)_2$. The reactant $CHR^2=CR^2COOH$ can then be mixed into this liquid phase rich in $R_fSO_2N(H)R^1N(R)_2$ whereupon the addition reaction can be carried out at the aforementioned reaction temperature range (above about 90° C.) to produce the desired product $R_fSO_2N(CHR^2-CHR^2COO-)R^1N+(R)_2H$.

The $CHR^2=CR^2COOH$ reactant can be used in sufficient stoichiometric excess to assure that a high percent, typically at least 95%, of the reactant $R_fSO_2N(H)R^1N(R)_2$ has reacted, but yet the amount of $CHR^2=CR^2COOH$ present preferably should be low enough to assure that the yield of the desired product, $R_fSO_2N(CHR^2-CHR^2COO-)R^1N+(R)_2H$ comprises at least 50 percent by weight, typically 70 to 90 percent by weight, of the total product resulting from said second reaction. The process of the invention does not depend on use of chlorine containing, corrosive compounds.

A specific process of the present invention is the synthesis of fluorochemical surfactant, a fluoroaliphatic aminocarboxylate,

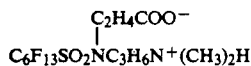
(II)

N-(2-carboxyethyl)-N-[3-(N',N'-dimethylamino)propyl] perfluorohexane sulfonamide. This compound has particular utility as an amphoteric fluorochemical surfactant for aqueous film-forming foam concentrates employed in extinguishing flammable liquid fires. Such concentrates are typically diluted with water to form a premix, which upon aeration produces an aqueous film-forming foam having excellent fire extinguishing properties, particularly for flammable liquid fires.

The novel process of the invention for synthesizing the above referenced compound (II) comprises a two-reaction sequence and can be conveniently carried out in the same reaction vessel. In the first (condensation) reaction (a), $C_6F_{13}SO_2F$, perfluorohexanesulfonyl fluoride, is reacted with an excess amount of $H_2NC_3H_6N(CH_3)_2$, 3-N',N'-dimethylaminopropylamine, advantageously at about 90° C. in an inert nitrogen atmosphere to produce an intermediate sulfonamide, namely $C_6F_{13}SO_2N(H)C_3H_6N(CH_3)_2$, N-[3-(N',N'-dimethylamino)propyl]perfluorohexane sulfonamide. An additional amount of another amine, e.g. triethylamine, $(C_2H_5)_3N$, is also included in the reaction mixture. The $(C_2H_5)_3N$ and excess $H_2NC_3H_6N(CH_3)_2$ react with hydrogen fluoride produced in the reaction to form amine hydrofluoride salts. Solvent, preferably toluene, is included in the reacting mixture to assure that all reactants and products remain in solution.

The $C_6F_{13}SO_2N(H)C_3H_6N(CH_3)_2$ intermediate compound produced in the first (condensation) reaction (a) is reacted in a second (addition) reaction (b) with acrylic acid, $CH_2=CHCOOH$, present in excess. It has been discovered that if this second reaction (b) is carried out at an elevated temperature, preferably between about 90° C. to 150° C., the acrylic acid will preferentially react with the sulfonamido nitrogen rather than with the tertiary amino nitrogen (of the dimethylamino group) of intermediate $C_6F_{13}SO_2N(H)C_3H_6N(CH_3)_2$. (Under ambient reaction conditions this reaction occurs mainly with the tertiary amino nitrogen rather than with the sulfonamido nitrogen yielding quaternary ammonium compounds.) The resulting product contains predominantly the desired perfluoroalkanesulfonamide (II), namely $C_6F_{13}SO_2N(C_2H_4COO-)C_3H_6N+(CH_3)_2H$, in yields greater than 50% by weight of the reaction product mixture and typically between about 70 to 90% by weight of the reaction product mixture. Small quantities of by-product, quaternary perfluoroalkanesulfonamide compounds are also produced in this second reaction.

The product mixture may typically contain about 20 percent by weight total of by-products and less than about 5 percent by weight of unreacted $C_6F_{13}SO_2N(H)C_3H_6N(CH_3)_2$.

The product mixture containing at least 50% by weight, typically between 70 to 90% by weight, of the preferred perfluoroalkanesulfonamide (II) can be used directly as the fluorochemical surfactant for use in aqueous film-forming foam concentrates employed in extinguishing flammable liquid fires.

The preferred perfluoroalkanesulfonamide (II) namely $C_6F_{13}SO_2N(C_2H_4COO-)C_3H_6N+(CH_3)_2H$, can be produced in nearly 100% purity, i.e. greater than 99.9% purity, by employing typically 99% or greater purity $C_6F_{13}SO_2N(H)C_3H_6N(CH_3)_2$ intermediate in the addition reaction (b) and recrystallizing out the preferred perfluoroalkanesulfonamide (II) from the resulting product mixture. In this case, the addition reaction (b) can be advantageously carried out using a minimum of excess acrylic acid, typically only about 8% excess.

It was surprising that the perfluorohexane sulfonamide (II) could be synthesized in high yield by the process of the invention since acrylic acid does not appreciably react at the sulfonamido nitrogen site at ambient conditions, but almost exclusively reacts at the tertiary amino nitrogen site yielding quaternary ammonium compounds. However, under elevated temperature of between about 90°-150° C., preferably between about 125°-135° C., we have discovered the addition of acrylic acid preferentially occurs at the sulfonamido nitrogen of the intermediate $C_6F_{13}SO_2N(H)C_3H_6N(CH_3)_2$ to produce the desired perfluorohexane sulfonamide (II) as the predominant reaction product.

By the synthesis route of the present invention the reaction of intermediate $C_6F_{13}SO_2N(H)C_3H_6N(CH_3)_2$ with acrylic acid, besides yielding the desired perfluorohexane sulfonamide (II), produces (in relatively small amounts) two quaternary ammonium fluorochemical by-products, namely:

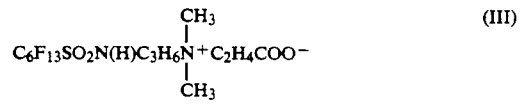
(III)

N-[3-(N',N'-dimethyl-N'-2-carboxyethylammonio)-propyl]perfluorohexane sulfonamide and;

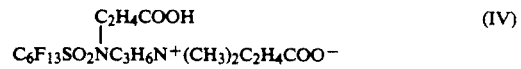
(IV)

N-[3-(N',N'-dimethyl-N'-2-carboxyethylammonio)-propyl]-N-(2-carboxyethyl)perfluorohexane sulfonamide.

These two quaternary ammonium fluorochemical by-products (III) and (IV) are amphoteric perfluorohexane sulfonamides which have utility as fluorochemical surfactants for fire extinguishing foamable concentrates but are not as desirable as the preferred non-quaternary sulfonamide (II), $C_6F_{13}SO_2N(C_2H_4COO-)C_3H_6N+(CH_3)_2H$.

We have found that the amount of by-product perfluorohexane sulfonamides, as represented by the above formulas (III) and (IV), and consequently the purity of the preferred specie, as represented by formula (II), can also be controlled by carrying out the addition reaction (b) between intermediate $C_6F_{13}SO_2N(H)C_3H_6N(CH_3)_2$ and acrylic acid at about 135° C. with varying excess amounts of acrylic acid. As the excess amount of acrylic acid is increased the concentration of the two by-product perfluorohexane sulfonamides (III) and (IV) in the reaction product will increase and the concentration of the preferred perfluorohexane sulfonamide (II) will decrease. It is not possible to obtain 0% concentration of by-product perfluorohexane sulfonamides (III) and (IV), even if a stoichiometric amount of acrylic acid is used at the desired reaction temperature of 135° C. Additionally there may be some intermediate $C_6F_{13}SO_2N(H)C_3H_6N(CH_3)_2$ left unreacted if a stoichiometric amount of acrylic acid is used. This is an undesirable result since this latter compound does not function as a fluorochemical surfactant at near neutral pH and would have a deleterious effect on foamability, stability and resultant fire extinguishment if used in an aqueous film-forming foamable concentrate for extinguishing flammable liquid fires. Thus applicants have determined that a practical optimum was to carry out the reaction of $C_6F_{13}SO_2N(H)C_3H_6N(CH_3)_2$ with acrylic acid at about 135° C., using 1.05 to 1.30 moles acrylic acid, preferably 1.15 to 1.25 moles acrylic acid for every 1 mole of $C_6F_{13}SO_2N(H)C_3H_6N(CH_3)_2$. Under these conditions there was sufficient excess acrylic acid (i.e. 25% excess) to assure that essentially all of the $C_6F_{13}SO_2N(H)C_3H_6N(CH_3)_2$ reacted. The resulting reaction product under these conditions will have a purity of about 70 to 90% of the desired specie of perfluorohexane sulfonamide (II).

The first reaction steps aforementioned can be represented as follows:

Condensation Reaction (a)

$C_6F_{13}SO_2F + 1.2\ H_2NC_3H_6N(CH_3)_2 + 0.8\ (C_2H_5)_3N$
$\rightarrow C_6F_{13}SO_2N(H)C_3H_6N(CH_3)_2 + $ Amine hydrofluorides.

The above Reaction (a) shows the condensation reaction of perfluorohexanesulfonyl fluoride with 20% excess of dimethylaminopropylamine to produce intermediate N-[3-(N',N'-dimethylamino)propyl]perfluorohexane sulfonamide. The dimethylaminopropylamine may typically be present in 10% to 30% stoichiometric excess. This reaction is carried out in a stainless steel reaction vessel advantageously at about 90° C. in an inert atmosphere, e.g. nitrogen, in the presence of toluene. The toluene is used as a solvent to solubilize all reactants and products at the reaction temperature of 90° C., allowing for homogeneous reaction conditions and for shorter reaction time. Hydrogen fluoride is produced from the reaction of $C_6F_{13}SO_2F$ and $H_2NC_3H_6N(CH_3)_2$. As the hydrogen fluoride is produced it reacts with $H_2NC_3H_6N(CH_3)_2$ (dimethylaminopropylamine) which is present in excess, and also with $(C_2H_5)_3N$ (triethylamine) to produce amine hydrofluoride salts. The reaction for scavenging hydrogen fluoride by triethylamine and dimethylaminopropylamine can be represented by the following reactions:

$H_2NC_3H_6NC_3H_6N(CH_3)_2 + HF \longrightarrow$ $F^-H_3N^+C_3H_6N(CH_3)_2 + H_2NC_3H_6N^+(CH_3)_2HF^-$ $(C_2H_5)_3N + HF \longrightarrow (C_2H_5)_3N^+HF^-$ The products of the foregoing two reactions are the amine hydrofluoride salts referred to in Reaction (a). Reaction (a) is completed after a reaction period of about 3 hours at 90° C. after which hot deionized water at a temperature of about 95° C. is added to the reacted mixture and the mixture stirred for a few minutes. A dark aqueous bottom phase, which forms containing the amine hydrofluoride by-product components, is then drained off. The remaining top phase contains toluene and $C_6F_{13}SO_2N(H)C_3H_6N(CH_3)_2$ as well as any residual dimethylaminopropylamine, triethylamine and water. The toluene and residuals can be gradually distilled off from the remaining top phase by single stage (batch) distillation of the mixture at atmospheric pressure by gradually raising the temperature of the mixture from about 90° C. until a final boiling temperature of about 135° C. is reached. The overhead vapor distillate contains toluene, residual water and amine while the remaining distill and contains the intermediate sulfonamide $C_6F_{13}SO_2N(H)C_3H_6N(CH_3)_2$ in greater than 90% purity.

The reaction of intermediate sulfonamide $C_6F_{13}SO_2N(H)C_3H_6N(CH_3)_2$, (at least about 90% purity) with acrylic acid can be represented by the second reaction as follows:

Addition Reaction (b)

$C_6F_{13}SO_2N(H)C_3H_6N(CH_3)_2 + 1.25\ CH_2{=}CHCOOH \longrightarrow$ $\underset{\text{(Principal product)}}{\overset{\overset{C_2H_4COO^-}{|}}{C_6F_{13}SO_2NC_3H_6N^+(CH_3)_2H}}$ (III)

plus $\underset{\text{(By-product)}}{\overset{\overset{CH_3}{|}}{C_6F_{13}SO_2N(H)C_3H_6\overset{|}{N}{}^+C_2H_4COO^-}}$ (III)

plus $\underset{\text{(By-product)}}{\overset{\overset{C_2H_4COOH}{|}}{C_6F_{13}SO_2NC_3H_6N^+(CH_3)_2C_2H_4COO^-}}$ (IV)

The acrylic acid should be in sufficient excess to assure that at least 95% of the intermediate sulfonamide, $C_6F_{13}SO_2N(H)C_3H_6N(CH_3)_2$, has reacted. Typically the acrylic acid is present in stoichiometric excess of between about 5 to 30 percent, preferably 15-25%. Reaction (b) may be carried out at a desired reaction temperature of between about 130° C. to 135° C. for about 10 hours in an atmosphere of 90% nitrogen and 10% oxygen by volume. Desirable results are obtained if the acrylic acid and intermediate sulfonamide $C_6F_{13}SO_2N(H)C_3H_6N(CH_3)_2$ reactants are present in the reaction mixture in a molar ratio of about 1.25:1. At this ratio the acrylic acid is in sufficient excess to assure that at least about 95 percent of the intermediate sulfonamide, $C_6F_{13}SO_2N(H)C_3H_6N(CH_3)_2$, will be reacted, but yet the amount of acrylic acid present is low enough to assure that good yields, typically between about 70 to 90% by weight of the desired perfluorohexane sulfonamide (II), namely $C_6F_{13}SO_2N(C_2H_4COO^-)C_3H_6N^+(CH_3)_2H$, is produced.

The preferred perfluoroalkanesulfonamide amphoteric product (II), namely $C_6F_{13}SO_2N(C_2H_4COO^-)C_3H_6N^+(CH_3)_2H$, can be produced in nearly 100% purity, e.g. greater than 99.9% purity. This can be accomplished by employing high purity, e.g. 99% or greater purity, $C_6F_{13}SO_2N(H)C_3H_6N(CH_3)_2$ intermediate in Reaction (b) and by using less than about 10% excess acrylic acid (typically about 8% stoichiometric excess acrylic acid) and recrystallizing product (II) from isopropyl alcohol.

However, it has been determined that 100% yield of the desired perfluorohexane sulfonamide (II) is not required but that yields as low as 50% by weight of this compound, preferably between 70 to 90% (the remainder comprising fluorochemical surfactant by-products (III) and (IV)), produce excellent fluorochemical surfactant mixtures for use in aqueous film-forming foamable concentrates for extinguishing flammable liquid fires.

A working example of the process of synthesis of the invention is given as follows:

Example 1

Step A.

A mixture of dimethylaminopropylamine, $H_2NC_3H_6N(CH_3)_2$ (12.2 g, 0.12 mole), triethylamine, $(C_2H_5)_3N$ (8.1 g, 0.08 mole) and toluene (60 g) was first prepared at ambient temperature and about atmospheric pressure in an inert atmosphere of nitrogen. To this mixture was added perfluorohexanesulfonyl fluoride, $C_6F_{13}SO_2F$ (41.0 g, 0.10 mole). The total mixture was then heated in a stainless steel reaction vessel at 90° C. for a period of about 3 hours forming a homogeneous reactant solution. During this period the aforementioned Reaction (a) takes place to produce intermediate N-[3-(N′,N′-dimethylamino)propyl]perfluorohexane sulfonamide, $C_6F_{13}SO_2N(H)C_3H_6N(CH_3)_2$.

The toluene was used in the reaction mixture as a solvent to solubilize all reactants and products (Reaction (a)) at the desired reaction temperature of 90° C. The excess amine, namely dimethylaminopropylamine and triethylamine, present in the reaction mixture functioned as a scavenger, i.e., to convert the hydrogen fluoride reaction by-product to amine hydrofluoride salts.

Step B

Hot deionized water (15 g) at a temperature of 95° C. was then added to the product mixture resulting from Step A, and the mixture was vigorously stirred for about 5 minutes while maintaining the mixture at a temperature of between about 85° to 90° C. This temperature level was required to keep all components in solution. At the end of this period the stirring was stopped and the product mixture described in Step A separated into two immiscible liquid phases, namely a top organic phase and a dark aqueous bottom phase. The top organic phase contained toluene, residual dimethylaminopropylamine and residual triethylamine, residual water and the desired intermediate sulfonamide product $C_6F_{13}SO_2N(H)C_3H_6N(CH_3)_2$. The dark bottom aqueous phase contained the amine hydrofluoride by-product salts and was simply removed by draining it from the reaction vessel. The toluene, residual water, and residual dimethylaminopropylamine and triethylamine were then distilled off from the remaining liquid phase mixture. The distillation was carried out as a batch distillation at atmospheric pressure by gradually raising the temperature of the remaining liquid phase mixture from about 90° C. until an end point boiling temperature of about 135° C. was reached. The overhead vapor distillate contained toluene, and residual water and amines (dimethylaminopropylamine and triethylamine). The overhead distillate was condensed and removed from the system using a water cooled condenser. After the distillation, the distilland remaining in the vessel contained the intermediate sulfonamide: $C_6F_{13}SO_2N(H)C_3H_6N(CH_3)_2$ in greater than 90% purity.

Step C

The distilland from Step B containing greater than 90% $C_6F_{13}SO_2N(H)C_3H_6N(CH_3)_2$ was then cooled to about 125° C. Phenothiazine (0.06 g, 1000 ppm) a free radical polymerization inhibitor and acrylic acid (9.0 g, 0.125 mole) containing 200 ppm p-methoxyphenol polymerization inhibitor were then added to the distilland mixture to form a reaction mixture which was subsequently heated and maintained at a reaction temperature between about 130° to 135° C. for 10 hours under an atmosphere of 90% nitrogen and 10% oxygen at about atmospheric pressure. (The phenothiazine and p-methoxyphenol along with the oxygen/nitrogen atmosphere prevent free radical polymerization side reactions of acrylic acid.) After reaction conditions were maintained at about 130° to 135° C. for about 10 hours, nuclear magnetic resonance (NMR) spectrometry analysis indicated the reaction was complete (Reaction (b)). The NMR analysis revealed formation of final product which contained less than 5 percent by weight of intermediate $C_6F_{13}SO_2N(H)C_3H_6N(CH_3)_2$. (Higher level concentration of this intermediate in the final product mixture is generally undesirable since it could interfere with the foaming characteristics and possibly other properties of the product mixture.) The mixture was cooled to 100° C. and residual toluene and residual acrylic acid were distilled off under reduced pressure (15 torr) at 95°–100° C. Butyl Carbitol (18.8 g) and deionized water (50.2 g) were added and the resulting mixture was stirred for 10 minutes until homogeneous to give a clear, light amber colored solution (45% solids/15% butyl Carbitol/40% water). The resulting product was a solution containing the preferred perfluorohexane sulfonamide (II), namely $C_6F_{13}SO_2N(C_2H_4COO-)C_3H_6N+(CH_3)_2H$, which comprised about 75 percent by weight of the product solids. The product solids also contained about 20 percent by weight (total) of aforementioned by-product quaternary ammonium perfluorohexane sulfonamides (III) and (IV), namely $C_6F_{13}SO_2N(H)C_3H_6N+(C_2H_4COO-)(CH_3)_2$ and $C_6F_{13}SO_2N(C_2H_4COOH)C_3H_6N+(C_2H_4COO-)(CH_3)_2$, as well as about 5 percent by weight or less of unreacted $C_6F_{13}SO_2N(H)C_3H_6N(CH_3)_2$.

This final product mixture exhibits excellent foaming and film-forming properties that lend to its use as a fluorochemical surfactant for aqueous film-forming foam concentrates employed in extinguishing flammable liquid fires.

EXAMPLE 2

The following synthetic procedure resulted in a product containing nearly 100% purity, e.g. greater than 99% purity, of the desired perfluorohexanesulfonamide (II), namely $C_6F_{13}SO_2N(C_2H_4COO-)C_3H_6N+(CH_3)_2H$, and essentially no other by-product perfluoralkanesulfonamide surfactant specie.

Step A

A solution of dimethylaminopropylamine (61.2 g, 0.66 mole) in toluene (300 g) was first formed at ambient temperature. To this solution was added perfluorohexanesulfonyl fluoride (123 g, 0.30 mole) and the total mixture was then heated for 3 hours at 90° C.

Step B

Hot deionized water (75 g) at a temperature of 95° C. was then added to the reaction mixture from Step A and vigorously stirred for 5 minutes while maintaining the mixture at a temperature between about 85° to 90° C. At the end of this period, the stirring was stopped and the reaction mixture separated into two immiscible liquid phases, a top toluene product solution phase and aqueous bottom phase. The bottom phase contained dimethylaminopropylamine hydrofluoride by-product and was drained off. This washing step was repeated two additional times, employing 75 g hot deionized water each time. After the final bottom aqueous phase was drained off, the organic liquid phase remaining contained toluene, $C_6F_{13}SO_2N(H)C_3H_6N(CH_3)_2$ and residual water. This liquid phase was cooled to ambient temperature and a white crystalline product separated out. The crystalline product was collected by filtration, washed with an additional portion of toluene (50 g) and air dried to give a white crystalline solid (123 g). This crystalline solid was analyzed by NMR (nuclear magnetic resonance) spectrometry and was identified as $C_6F_{13}SO_2N(H)C_3H_6N(CH_3)_2$, N-[3-(N',N'-dimethylamino)propyl]perfluorohexane sulfonamide, having a purity of greater than 99 percent and a melting point of 125° to 128° C.

Step C

A portion of the crystalline $C_6F_{13}SO_2N(H)C_3H_6N(CH_3)_2$ (12.1 g, 0.025 mole) from Step B was mixed with acrylic acid (1.95 g, 0.027 mole), stabilized with 200 ppm p-methoxyphenol. (The acrylic acid was thus present in only about 8 percent excess.) This mixture was heated to a reaction temperature of about 135° C. in a glass reaction vessel and was maintained at that temperature in an atmosphere of air for about 10 hours. Thereupon the resulting product mixture was cooled to ambient temperature to yield a light beige brittle solid. Proton and fluorine NMR spectrometry analysis showed that the brittle solid contained 95 percent by weight of the desired perfluoroalkanesulfonamide amphoteric surfactant (II), namely $C_6F_{13}SO_2N(C_2H_4COO-)C_3H_6N+(CH_3)_2H$, with only 5 percent by weight of the quaternary perfluoroalkanesulfonamide by-product (III), $C_6F_{13}SO_2N(H)C_3H_6N+(CH_3)_2C_2H_4COO-$. Recrystallization of a portion of the brittle solid product (8 g) from isopropylalcohol (45 mL) yielded 6.2 g of the desired compound (II), m.p. 165°-168° C., in nearly 100% purity, i.e. greater than 99% purity. The foregoing example demonstrates that it is possible to achieve nearly 100% purity of the desired perfluoroalkanesulfonamide amphoteric surfactant (II) employing the reaction steps of the present invention. However, the process described in Example 1 is preferred, since it lends itself better to economical scale-up and commercialization. The fluorochemical surfactant product mixture resulting from the process of Example 1 is thus preferred. Although the Example 1 product mixture contained lower yield of the most desired perfluoroalkanesulfonamide amphoteric surfactant (II), such product nonetheless exhibits excellent properties as a fluorochemical surfactant mixture for use in aqueous film-forming foamable fire extinguishing concentrates.

The above described method of synthesis and procedure can be employed more generally to produce a compound represented by the formula

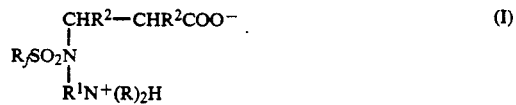

from starting reactants represented by the formulas
$R_fSO_2F$, $H_2NR^1N(R)_2$ and $CHR^2=CHR^2COOH$ where:
- $R^1$ represents a divalent organic radical preferably free from non-aromatic unsaturation, e.g., alkylene, (e.g. ethylene or propylene) oxyalkylene, arylene, alkarylene or aralkylene, of 2 to 12 carbon atoms and preferably 2 to 6 carbon atoms, which may be substituted, e.g. with non-active hydrogen-containing substituents;
- each R represents like or different groups of 1 to 12 carbon atoms and preferably 1 to 4 carbon atoms each of which group is independently selected from alkyl, substituted alkyl, aryl, alkaryl, and aralkyl (e.g. benzyl), or the two R groups along with attached nitrogen can form a heterocyclic ring (e.g. morpholine);
- each $R^2$ is independently H or $CH_3$, preferably H; and
- $R_f$ is a fluoroaliphatic group, namely a fluorinated, stable, inert, preferably saturated, non-polar monovalent aliphatic radical. It can be straight chain, branched chain, or cyclic or combinations thereof. It can contain catenary heteroatoms, bonded only to carbon atoms, such as oxygen, divalent or hexavalent sulfur, or nitrogen. $R_f$ is preferably a fully fluorinated radical, but hydrogen or chlorine atoms can be present as substituents provided that not more than one atom of either is present for every two carbon atoms. The $R_f$ radical has at least 3 carbon atoms, preferably 3 to 20 carbon atoms and most preferably about 4 to about 10 carbon atoms, and preferably contains about 40% to about 78% fluorine by weight, more preferably about 50% to about 78% fluorine by weight. The terminal portion of the $R_f$ radical is a perfluorinated moiety which will preferably contain at least 7 fluorine atoms, e.g. $CF_3CF_2CF_2-$, $(CF_3)_2CF-$, $F_5SCF_2-$, or the like. The preferred $R_f$ radicals are fully or substantially fluorinated and are preferably those perfluorinated aliphatic radicals of the formula $C_aF_{2a+1}-$.

The first reaction as alluded to in the foregoing then becomes (a):

The second reaction alluded to in the foregoing becomes (b):

$$R_fSO_2N\begin{matrix}CHR^2-CHR^2COO^-\\|\\R^1N^+(R)_2H\end{matrix}$$

Although the first reaction (a) is most preferably carried out in the presence of a tertiary amine such as triethylamine, other tertiary amines, for example, trimethylamine and tetramethylethylenediamine, can be used.

The general procedure as described with respect to the specific embodiments, including the addition of polymerization inhibitors such as phenothiazine to the second reaction, are still applicable. The above described method of employing a suitable solvent such as toluene to solubilize all the reactants and products in the first reaction and subsequent distillation to remove the solvent leaving a liquid phase containing at least 90% by weight $R_fSO_2N(H)R^1N(R)_2$ will still be applicable. This liquid phase rich in $R_fSO_2N(H)R^1N(R)_2$ is then mixed with $CHR^2=CR^2COOH$ whereupon the second reaction is carried out in the manner described in the foregoing preferred embodiment. Also, the reactant $CHR^2=CR^2COOH$ should be in sufficient stoichiometric excess to assure that at least about 95% of the intermediate $R_fSO_2N(H)R^1N(R)_2$ has reacted, but yet the amount of $CHR^2=CR^2COOH$ present should be low enough to assure that the yield of the desired product $R_fSO_2N(CHR^2-CHR^2COO-)R^1N+(R)_2H$ comprises at least 50 percent by weight, typically 70 to 90 percent by weight of the total product produced in the second reaction. It will be appreciated that the optimum reaction temperatures for the first and second reactions will depend on the reactants and products and such reaction temperatures can be adjusted accordingly. The first reaction will typically be carried out at temperatures above 80° C., typically between about 85° and 95° C., and the second reaction at temperatures above 90° C., typically between about 125 and 140° C. The reactions may be carried out without catalyst.

Representative amphoteric fluoroaliphatic aminocarboxylates of the general formula (I), above referenced, include the following compounds:

$$C_8F_{17}SO_2N\begin{matrix}C_2H_4COO^-\\|\\C_3H_6N^+(CH_3)_2H\end{matrix}$$

$$C_8F_{17}SO_2N\begin{matrix}C_2H_4COO^-\\|\\C_3H_6N^+(C_2H_5)_2H\end{matrix}$$

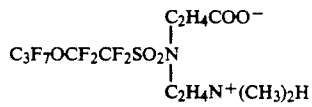

$C_8F_{17}C_2H_4SO_2NC_3H_6N^+(CH_3)_2H$ with $C_2H_4COO^-$ $$C_7F_{15}SO_2N\begin{matrix}C_2H_4COO^-\\|\\CH_2C_6H_4CH_2N^+(CH_3)_2H\end{matrix}$$

$$C_8F_{17}SO_2N\begin{matrix}C_2H_4COO^-\\|\\C_2H_4OC_2H_4N^+(CH_3)_2H\end{matrix}$$

$$C_6F_{13}SO_2N\begin{matrix}C_2H_4COO^-\\|\\C_3H_6N^+(CH_3)_2H\end{matrix}$$

$$C_8F_{17}SO_2N\begin{matrix}C_2H_4COO^-\\|\\C_3H_6N^+(C_4H_9)_2H\end{matrix}$$

$C_{10}F_{19}OC_6H_4SO_2N(C_2H_4COO^-)C_3H_6N^+(CH_3)_2H$ $C_6F_{13}SO_3C_6H_4SO_2N(C_2H_4COO^-)C_3H_6N^+(CH_3)_2H$ $$C_6F_{13}SO_2N\begin{matrix}CH_2CH(CH_3)COO^-\\|\\C_3H_6N^+(CH_3)_2H\end{matrix}$$

$$C_8F_{17}SO_2N\begin{matrix}CH(CH_3)CH_2COO^-\\|\\C_3H_6N^+(C_4H_9)_2H\end{matrix}$$

$$C_3F_7OCF_2CF_2SO_2N\begin{matrix}C_2H_4COO^-\\|\\C_2H_4N^+(CH_3)_2H\end{matrix}$$

$$C_6F_{13}SO_2N\begin{matrix}C_2H_4COO^-\\|\\C_2H_4N^+(CH_2C_6H_5)_2H\end{matrix}$$

$$C_6F_{13}SO_2N\begin{matrix}C_2H_4COO^-\\|\\C_6H_{12}N^+(C_2H_5)_2H\end{matrix}$$

$$SF_5C_4F_8SO_2N\begin{matrix}C_2H_4COO^-\\|\\C_3H_6N^+(CH_3)_2H\end{matrix}$$

The fluoroaliphatic amphoteric surfactant compounds of this invention advantageously should have a balance of properties between the non-polar fluoroaliphatic radical(s), the polar water soluble group(s), i.e. the anionic and cationic groups present, and any organic linking groups in the surfactant compound, so as to provide solubility in water at 25° C. of at least 0.01 percent by weight, preferably at least about 0.05 percent by weight. In order to function effectively as a film-spreading agent, the surfactant must be sufficiently surface active to provide a surface tension of less than about 28 dynes/cm, preferably less than 23 dynes/cm, in aqueous solution at a concentration of about 0.05 to 0.10 percent by weight or less.

If the fluoroaliphatic surfactant is too soluble in hydrocarbon liquid, it will be extracted too rapidly from the aqueous film to provide sufficiently durable coverage. In general, this requires the presence of at least about 20 percent by weight of fluorine in the fluoroaliphatic radical portion of the surfactant.

Although the present invention has been described with reference to specific embodiments, it will be appreciated that variations are possible without departing from the scope and concept of the invention. The invention therefore is not intended to be limited to the preferred embodiments but rather is defined by the claims and equivalents thereof.

We claim:

1. A process for the synthesis of the class of compounds represented by the formula:

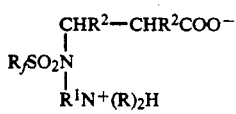

wherein:
R$_f$ is a fluoroaliphatic radical;
R$^1$ is a divalent organic radical selected from the group consisting of alkylene, oxyalkylene, arylene, alkarylene, and aralkylene;
R represents like or different groups each of which is independently selected from the group consisting of alkyl, aryl, alkaryl, and aralkyl, or the two R groups along with attached nitrogen can form a heterocyclic ring;
R$^2$ is independently selected from the group consisting of hydrogen and methyl;
said process of synthesis comprising the addition reaction (b) of R$_f$SO$_2$N(H)R$^1$N(R)$_2$ with CHR$^2$=CR$^2$COOH to produce said compound

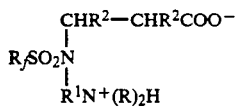

wherein said reaction (b) is carried out at a temperature above about 90° C.

2. The process of claim 1 further comprising the condensation reaction (a) of the compounds R$_f$SO$_2$F and H$_2$NR$^1$N(R)$_2$ in solution to produce said compound R$_f$SO$_2$N(H)R$^1$N(R)$_2$ employed in said addition reaction (b).

3. The process of claim 2 wherein reaction (a) is carried out at a temperature above about 80° C.

4. The process of claim 2 wherein reaction (b) is carried out at a temperature between about 90° C. 50° C. and reaction (a) is carried out at a temperature between about 80° C. to 95° C.

5. A process for synthesis of the compound represented by the formula:

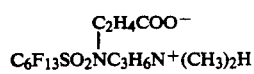

comprising the addition reaction (b) of the compounds C$_6$F$_{13}$SO$_2$N(H)C$_3$H$_6$N(CH$_3$)$_2$ and CH$_2$=CHCOOH to produce said compound.

6. The process of claim 5 which further comprising the condensation reaction (a) of the compounds C$_6$F$_{13}$SO$_2$F and H$_2$NC$_3$H$_6$N(CH$_3$)$_2$ in solution to produce said compound C$_6$F$_{13}$SO$_2$N(H)C$_3$H$_6$N(CH$_3$)$_2$ employed in addition reaction (b).

7. The process of claim 5 wherein reaction (b) is carried out at temperatures above about 90° C.

8. The process of claim 6 wherein reaction (a) is carried out at a temperature above about 80° C.

9. The process of claim 6 wherein reaction (b) is carried out at a temperature between about 90° C. and 150° C. and reaction (a) is carried out at a temperature between about 80° C. to 95° C.

10. The process of claim 5 wherein the percentage of compound C$_6$F$_{13}$SO$_2$N(H)C$_3$H$_6$N(CH$_3$)$_2$ reacted with CH$_2$=CHCOOH in addition reaction (b) is controlled by the amount of stoichiometric excess of CH$_2$=CHCOOH present.

11. The process of claim 10 wherein the CH$_2$=CHCOOH reactant is sufficiently in stoichiometric excess to assure that at least 95% of the compound C$_6$F$_{13}$SO$_2$N(H)C$_3$H$_6$N(CH$_3$)$_2$ has reacted.

12. The process of claim 11 wherein the CH$_2$=CHCOOH is present in the reaction mixture in stoichiometric excess of between about 5 to 30 percent.

13. The process of claim 12 wherein the compound

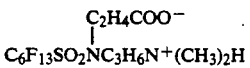

comprises at least 50 percent by weight all reaction products formed in addition reaction (a).

14. The process of claim 12 wherein the compound

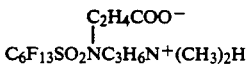

comprises between about 50 to 90 percent by weight of all reaction products formed in addition reaction (b).

15. The process of claim 6 wherein said solution containing reactants C$_6$F$_{13}$SO$_2$F and H$_2$NC$_3$H$_6$N(CH$_3$)$_2$ comprises a solvent to solubilize said reactants and reaction products at reaction temperature.

16. The process of claim 15 wherein the solvent comprises toluene.

17. The process of claim 13 further comprising the steps:
(c) after said reaction step (a), washing the resulting solution with water to remove amine hydrofluoride by-product formed during said reaction step (a),
(d) after said washing step (c), removing an aqueous bottoms phase containing said amine hydrofluoride by-product and
(e) distilling solvent from the remaining liquid phase to increase the percent by weight of the compound C$_6$F$_{13}$SO$_2$N(H)C$_3$H$_6$N(CH$_3$)$_2$ in said remaining liquid phase.

18. The process of claim 6 wherein said solution comprising reactants C$_6$F$_{13}$SO$_2$F and H$_2$NC$_3$H$_6$N(CH$_3$)$_2$ further comprises one other tertiary amine compound to help remove hydrogen fluoride by-product formed during the reaction (a).

19. The process of claim 1 wherein the percentage of compound R$_f$SO$_2$N(H)R$^1$N(R)$_2$ reacted in step (b) is controlled by the amount of stoichiometric excess of CHR$^2$=CR$^2$COOH present.

20. The process of claim 2 wherein said solution containing reactants R$_f$SO$_2$F and H$_2$NR$^1$N(R)$_2$ comprises a solvent to solubilize said reactants and reaction products at reaction temperature.

21. The process of claim 20 further comprising the steps:

(c) after said reaction step (a), washing the resulting solution with water to remove amine hydrofluoride by-product formed during said reaction step (a), (d) after said washing step (c), removing an aqueous bottoms phase containing said amine hydrofluoride by-product and (e) distilling solvent from the remaining liquid phase to increase the percent by weight of the compound $R_fSO_2N(H)R^1N(R)_2$ in said remaining liquid phase.

* * * * *